(12) United States Patent
Landis (10) Patent No.: US 7,156,096 B2
(45) Date of Patent: Jan. 2, 2007

(54) DYNAMIC INFANT NASAL CPAP SYSTEM AND METHOD

(76) Inventor: Robert M. Landis, 1130 Puddingstone Rd., Mountainside, NJ (US) 07092

( * ) Notice: Subject to any disclaimer, the term of this patent is extended or adjusted under 35 U.S.C. 154(b) by 312 days.

(21) Appl. No.: 10/618,799

(22) Filed: Jul. 14, 2003

(65) Prior Publication Data

US 2004/0065330 A1  Apr. 8, 2004

Related U.S. Application Data

(60) Provisional application No. 60/395,816, filed on Jul. 15, 2002.

(51) Int. Cl.
 A61M 16/00 (2006.01)
 A62B 7/00 (2006.01)
(52) U.S. Cl. .............. 128/204.18; 128/207.13
(58) Field of Classification Search .......... 128/206.11, 128/206.21, 206.24, 206.27, 207.11, 207.12, 128/207.13, 207.18, 206.18, 206.15, 204.18, 128/203.22
See application file for complete search history.

(56) References Cited

U.S. PATENT DOCUMENTS

| | | | |
|---|---|---|---|
| 4,018,221 A | 4/1977 | Rennie | |
| 4,156,426 A | 5/1979 | Gold | |
| 4,249,527 A | 2/1981 | Ko et al. | |
| 4,261,355 A | 4/1981 | Glazener | |
| 4,278,082 A | 7/1981 | Blackmer | |
| 4,774,946 A | 10/1988 | Ackerman et al. | |
| 4,782,832 A * | 11/1988 | Trimble et al. ........ | 128/207.18 |
| 4,821,709 A | 4/1989 | Jensen | |
| 4,821,736 A | 4/1989 | Watson | |
| 4,919,128 A | 4/1990 | Kopala et al. | |
| 4,944,310 A | 7/1990 | Sullivan | |
| 5,040,532 A | 8/1991 | Alfery | |
| 5,042,478 A | 8/1991 | Kopala et al. | |
| 5,117,819 A | 6/1992 | Servidio et al. | |
| 5,188,101 A | 2/1993 | Tumolo | |
| 5,193,532 A | 3/1993 | Moa et al. | |
| 5,220,699 A | 6/1993 | Farris | |
| 5,243,971 A | 9/1993 | Sullivan et al. | |
| 5,269,296 A | 12/1993 | Landis | |
| 5,271,391 A | 12/1993 | Graves | |
| 5,361,416 A | 11/1994 | Petrie et al. | |
| 5,477,852 A | 12/1995 | Landis et al. | |
| 5,687,715 A | 11/1997 | Landis et al. | |
| 5,687,743 A | 11/1997 | Goodwin | |
| 5,724,965 A | 3/1998 | Handke et al. | |
| 5,975,077 A | 11/1999 | Hofstetter et al. | |
| 6,119,693 A | 9/2000 | Kwok et al. | |
| 6,119,694 A | 9/2000 | Correa et al. | |
| 6,192,886 B1 | 2/2001 | Rudolph | |
| 6,418,929 B1 | 7/2002 | Norfleet | |
| 6,422,238 B1 | 7/2002 | Lithgow | |
| 6,427,694 B1 | 8/2002 | Hecker et al. | |
| 6,431,172 B1 | 8/2002 | Bordewick | |
| 6,439,230 B1 | 8/2002 | Gunaratnam et al. | |
| 6,439,234 B1 | 8/2002 | Curti et al. | |
| 6,470,886 B1 | 10/2002 | Jestrabek-Hart | |
| 6,595,215 B1 * | 7/2003 | Wood ................ | 128/207.18 |
| 6,769,432 B1 * | 8/2004 | Keifer ................ | 128/206.11 |
| 6,823,865 B1 * | 11/2004 | Drew et al. ........... | 128/204.18 |

* cited by examiner

*Primary Examiner*—Henry Bennett
*Assistant Examiner*—Shumaya B. Ali (57) ABSTRACT

Continuous positive airway pressure systems are provided including an interface defining a plenum chamber therein, and a pair of nasal cannulas connected to and in fluid communication with the plenum chamber of the interface. The nasal cannulas are configured and dimensioned to deliver pressurized air from the plenum chamber to the nares of a patient, wherein each nasal cannula is capable of off axis movement and/or pivoting.

13 Claims, 11 Drawing Sheets

DYNAMIC INFANT NASAL CPAP SYSTEM AND METHOD

CROSS-REFERENCE TO RELATED APPLICATIONS

The present application claims the benefit of and priority to U.S. Provisional Patent Application No. 60/395,816, filed on Jul. 15, 2002, the entire contents of which are hereby incorporated by reference.

BACKGROUND

1. Technical Field

The present disclosure relates generally to the field of respiratory therapy and, more particularly, to a continuous positive airway pressure system and methods used for delivering continuous positive airway pressure, via the nasal cannula, to premature infants suffering from Respiratory Distress Syndrome (RDS) or other respiratory ailments.

2. Background of Related Art

Infants born prematurely frequently suffer with increased work of breathing due to the immature lungs that have a propensity to collapse during exhalation and resist expansion during inhalation, commonly referred to as Respiratory Distress Syndrome (RDS). In contrast mature healthy lungs have a resiliency to remain inflated at the end of exhalation and expand with ease during inhalation. An infant's lung may also collapse due to airway obstruction or anatomical abnormalities.

One particular method of treatment of RDS involves the use of nasal cannula that fit sealingly into the nares and connected to a breathing system that generates a continuous flow of air with above atmospheric pressures, commonly referred to as Continuous Positive Airway Pressure (CPAP) therapy. The positive pressure is transmitted through the infant's airways and into the lungs thereby preventing collapse during exhalation and augmenting expansion during inhalation. The CPAP therapy is frequently administered for two to three days for twenty-four hours a day. The therapy improves oxygenation of the blood and reduces the work of breathing allowing the lungs to mature and grow.

The adverse events that arise from the application of these devices for the prescribed period of time are many fold. For example, the cannula are part of a rigid base that produces pressure points on tissue when there is not an exact fit; the cannula base connects directly to the supply tubing which is difficult to stabilize and movement can easily cause poor cannula alignment inside the nares; the cannula can become dislodged from the nares; abrasions can be caused in the nares from the cannula fitting too loosely; tissue perfusion can be cut off it the cannula fit too tightly which can lead to necrosis; if the cannula are too close to one another the nasal septum can be pinched, if the cannula are too far from one another pressure points can be created in the nares; if the device is heavy, "sand bagging" of the infant's head is required to prevent the infant's head from moving; head gear straps need to be tightly adjusted about the infant's head to prevent movement which in turn can cause "molding" of the infant's head; and all infant nasal CPAP devices are designed to be powered by a ventilator, flow meter or special driver all of which require "high pressure" compressed air and/or "high pressure" oxygen.

Recently, nasal CPAP or nCPAP has become more widely prescribed as the treatment of choice for premature infants suffering from Respiratory Disease Syndrome (RDS). As a result, there has been a rise in the adverse events related to the therapy of RDS. The severity of such adverse events range from mild (where the damage goes away on its own) to permanent (where the infant requires plastic surgery to repair the damage caused by the cannula).

The use of CPAP has also been extended into the treatment of neonatal problems other than respiratory distress syndrome, such as, for example, apnea of prematurity, patent ductus arteriosus, meconium aspiration syndrome and post-surgical cases.

Accordingly, the need exists for a device that can deliver nCPAP to premature infants in such a way so as to reduce and/or eliminate the adverse events listed above.

SUMMARY

The continuous positive airway pressure system, according to one aspect of the present disclosure, includes an interface defining a plenum chamber therein, wherein the interface is connectable to a ventilation circuit for delivering pressurized air to the plenum chamber, and a pair of nasal cannulas connected to and in fluid communication with the plenum chamber of the interface. The nasal cannulas are configured and dimensioned to deliver pressurized air from the plenum chamber to the nares of a patient. Each nasal cannula is capable of off axis movement and/or off axis pivoting, preferably, without kinking. It is envisioned that at least a portion of the interface is fabricated from elastic material. Preferably, the interface is fabricated from silicone. In certain embodiments the tip of each nasal cannula can be fluted.

The continuous positive airway pressure system further includes a conduit internally disposed within the interface. The conduit extends from the ventilation circuit to a location in close proximity to the nasal cannulas. The conduit is preferably flexible.

The continuous positive airway pressure system can further include an exhalation vent formed in a distal end of the interface. The exhalation vent is desirably sized to allow a sufficient volume of gas to pass therethrough to prevent rebreathing in any significant amount. The literature recommends the volume to be more that two times the patients exhaled minute volume. The continuous positive airway pressure system can further include a vent cover overlying the exhalation vent.

It is envisioned that the continuous positive airway pressure system further includes support stems disposed within the interface and about the nasal cannulas. The support stems maintain the nasal cannulas in fluid communication with the plenum chamber.

The continuous positive airway pressure system further includes a bonnet for mounting the system to the head of the patient. The bonnet includes a body portion with straps extending therefrom. The body portion includes at least one slit formed therein. Each strap can include one portion of a hook and loop fastener while the interface can include the other portion of the hook and loop fastener. In this manner, the bonnet can be releasably engaged with the one portion of the hook and loop fastener.

In another aspect of the present disclosure, an interface for use in a continuous positive airway pressure system is provided. The interface includes a plenum chamber having an elastic portion configured and adapted to be in fluid communication with a source for delivering pressurized air, and nasal interface structure extending from the plenum chamber and in fluid communication therewith.

Preferably, each nasal cannula includes an annular trough formed therearound and in a surface of the interface.

The interface can further include a conduit disposed within the plenum chamber. The conduit can extend through the plenum chamber to a location in close proximity with the nasal cannulas.

The interface can further include an exhalation vent extending into the plenum chamber. The exhalation vent is desirably sized to allow a sufficient volume of gas to pass therethrough to prevent rebreathing in any significant amount.

In certain embodiments, a distal end of the interface is provided with corrugations enabling the distal end of the interface to bend with respect to the remainder to the interface. Preferably, the conduit is in fluid communication with a source of pressurized air.

In certain embodiments the tip of each nasal cannula is fluted.

The elastic portions of the plenum chamber enhance and/or supplement the air pressure within the plenum chamber.

According to another aspect of the present disclosure, a method of treating with continuous positive airway pressure is provided. The method includes the step of providing a continuous positive airway pressure system. The system includes an interface defining a plenum chamber therein, wherein the interface is connectable to a ventilation circuit for delivering pressurized air to the plenum chamber, and a pair of nasal cannulas connected to and in fluid communication with the plenum chamber of the interface, the nasal cannula being configured and dimensioned to fit sealingly tight in the nares and deliver pressurized air from the plenum chamber to the nares of a patient, each nasal cannula being capable of off axis displacement.

The method further includes the steps of connecting the continuous positive airway pressure system to a source of pressurized air, inserting the nasal cannulas into the nares of the patient, and activating the source of pressurized air to supply positive air pressure to the nasal cannulas through the plenum chamber.

It is envisioned that the interface can include an exhalation vent formed therein for venting excess air pressure from the plenum chamber.

These and other advantages of the invention will become apparent to those skilled in the art from the foregoing general description of the following detailed disclosure, and from practice with the invention.

BRIEF DESCRIPTION OF THE DRAWINGS

By way of example only, preferred embodiments of the disclosure will be described with reference to the accompanying drawings, in which.

DETAILED DESCRIPTION OF PREFERRED EMBODIMENTS

Reference is now made specifically to the drawings in which identical or similar elements are designated by the same reference numerals throughout. In the drawings and in the description which follows, the term "proximal", as is traditional will refer to the end of the device or apparatus which is closest to the patient, while the term "distal" will refer to the end of the device or apparatus which is furthest from the patient.

Figure 1:
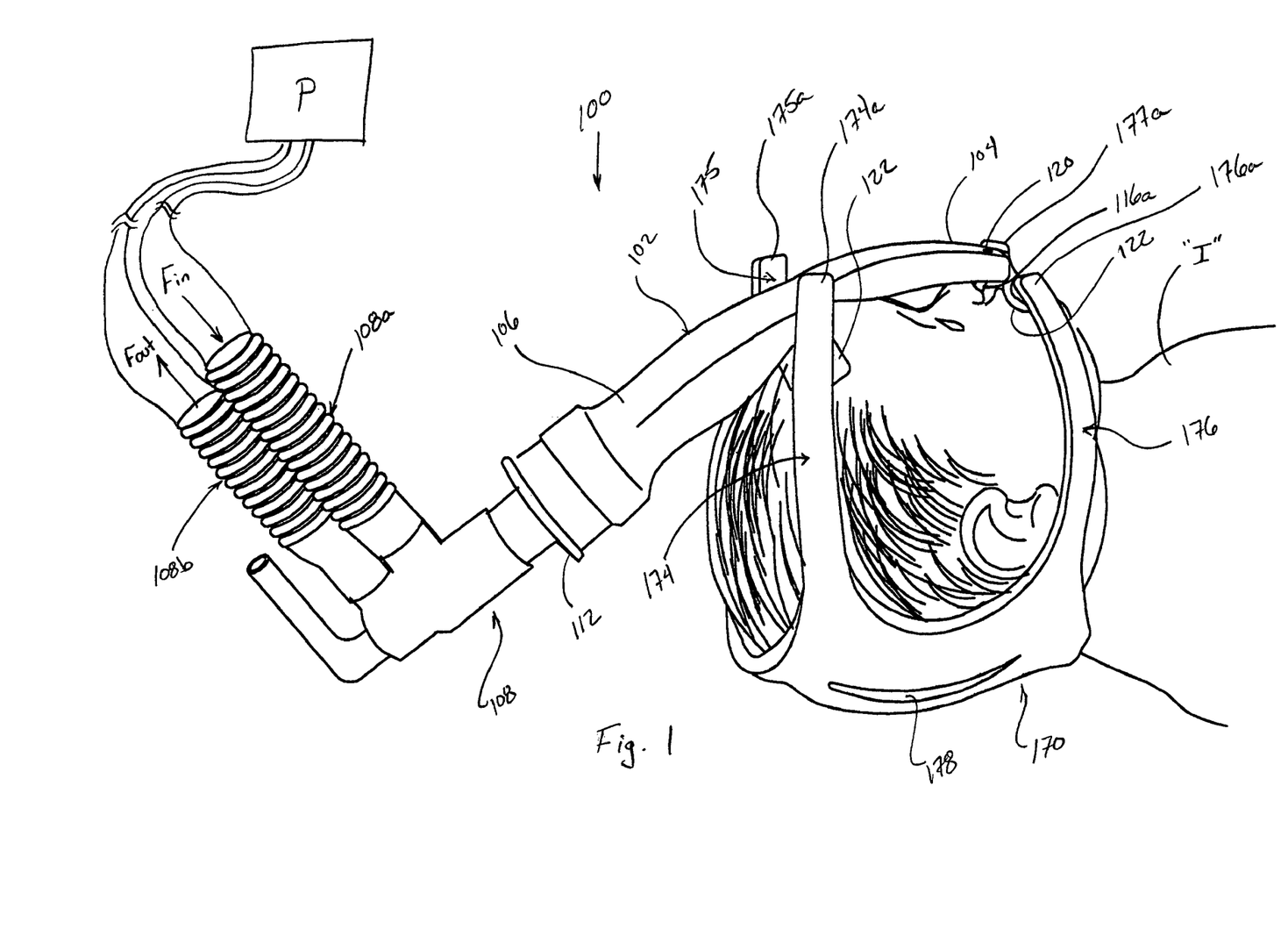
FIG. 1 is a perspective view of a continuous positive airway pressure system in accordance with an embodiment of the present disclosure, supported on the head of a patient and/or infant.

With reference to FIGS. 1–4, a continuous positive airway pressure system (CPAP) is shown generally as 100. In FIG. 1, CPAP 100 is shown in the operative position supported on a patient, preferably an infant "I". CPAP 100 includes a bladder-like interface 102 having a proximal end portion 104 and a distal end portion 106 configured and adapted to fluidly engage a ventilation circuit 108. Preferably, distal end portion 106 includes an opening 110 configured and dimensioned to receive a universal adapter 112, preferably a 15 mm adapter, of ventilation circuit 108.

Interface 102 defines a plenum chamber 114. Interface 102 is preferably fabricated from a resilient, elastic material which can be molded and/or formed into a desired shape and which retains its shape and still provides a degree of flexibility, resiliency and/or elasticity, such as, for example, silicone, rubber, polyethylene and the like.

Proximal end portion 104 includes a nasal interface structure for operatively engaging the nasal region (including the nares) of infant "I". Preferably, proximal end portion 104 includes a pair of nasal cannulas 116a, 116b extending therefrom. Preferably, nasal cannulas 116a, 116b are cantilevered from a lower surface 102a of interface 102. Nasal cannulas 116a, 116b are configured and dimensioned to be received, one each, in the nares of infant "I". Nasal cannulas 116a, 116b define respective lumens 118a, 118b which extend into plenum chamber 114 of interface 102. Preferably, nasal cannulas 116a, 116b are attached to lower surface 102a of interface 102 in such a manner that nasal cannulas 116a, 116b enjoy a degree of radial deflection about longitudinal axes thereof such that as infant "I" moves his/her head, nasal cannulas 116a, 116b will remain in and be guided by the nares of infant "I".

Proximal end portion 104 further includes an exhalation vent 120 formed in an upper surface 102b of interface 102. Preferably, as will be described in greater detail below, exhalation vent 120 is sized to permit more than two times the exhalation volume of infant "I" to escape therethrough with each exhalation of infant "I". In addition, exhalation vent 120 vents excess pressurized air from plenum chamber 114.

Continuous positive airway pressure system 100 further includes a plurality of tabs 122 extending therefrom. Preferably, each tab 122 includes a hook or loop portion 124a of a fastener element secured thereto. As will be described in greater detail below, hook or loop portion 124a is intended to releasably engage the other of the hook or loop portion provided on the distal end 174a–177a of straps 174–177 of a bonnet 170 which wraps around the head infant "I" and secures continuous positive airway pressure system 100 in position relative to infant "I".

In use, with continuous positive airway pressure system 100 in fluid communication with a source of air pressure "P" and with infant "I" wearing continuous positive airway pressure system 100 as shown in FIG. 1 (i.e., nasal cannulas 116a, 116b positioned in the nares of infant "I" and interface 102 extending over the forehead of infant "I", air is supplied to interface 102, from air pressure source "P" (e.g., a ventilator, a CPAP blower, etc.) via a first ventilation tube 108a of ventilation circuit 108 as indicated by the arrow $F_{in}$. The continuous flow of air into continuous positive airway pressure system 100 causes interface 102 to fill and expand. Air flow $F_{in}$ is then divided into several portions, a first portion which exits through exhalation vent 120, a second portion which exits through lumens 118a, 118b of nasal cannulas 116a, 116b, and a third portion which exits through a second ventilation tube 108b of ventilation circuit 108 as indicated by arrow $F_{out}$. Air flow $F_{out}$ is preferably regulated such that air flow $F_{in}$ is supplied at the desired rate.

In use, infant "I" inhales air from expanded pressurized interface 102 through nasal cannulas 116a, 116b and exhales back into interface 102. When infant "I" exhales, sufficient exhaled air is transmitted out of interface 102 through exhalation vent 120 to prevent $CO_2$ from building up and to reduce the rebreathing of exhaled air. As described above, preferably, exhalation vent 120 is sized such that more than two times the exhalation volume of infant "I" exits exhalation vent 120 on each exhalation of infant "I".

The elastic and expanding properties of interface 102 are efficacious in the delivery and administration of nasal CPAP therapy. Interface 102 is able to maintain CPAP levels in the upper airways of infant "I" as compared to other devices. In particular, during the inspiratory phase of respiration, interface 102 performs as a reservoir providing both volume and pressure to meet inspiratory needs, and during the exhalation phase of respiration, interface 102 receives and/or dissipates the exhalation without producing added resistance to infant "I". In other words, the elastic and expanding properties of interface 102 enhance and/or supplement the air flow in and out of plenum chamber 114.

Figure 2:
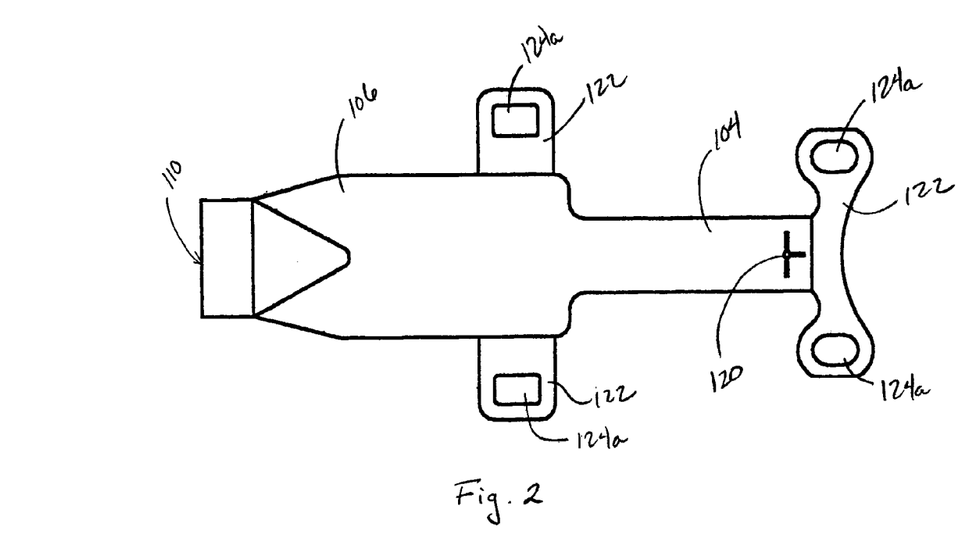
FIG. 2 is top plan view of the continuous positive airway pressure system of FIG. 1.

As seen in FIG. 2, distal end portion 106 has an enlarged cross sectional area as compared to proximal end portion 104. In particular, proximal end portion 104 has a width and distal end portion 106 has a width which is larger than the width of proximal end portion 104. The enlarged distal end portion 106 allows for improved visual observation of the respiratory function of infant "I" in that as infant "I" respires, distal end portion 106 of interface 102 will have a tendency to extend and contract an amount visible to the eye.

With reference to FIGS. 5–8, a continuous positive airway pressure system in accordance with an alternate embodiment of the present disclosure is shown generally as 200. Continuous positive airway pressure system 200 is similar to continuous positive airway pressure system 100 and will only be described in detail to the extent necessary to identify differences in construction and use.

Figure 5:
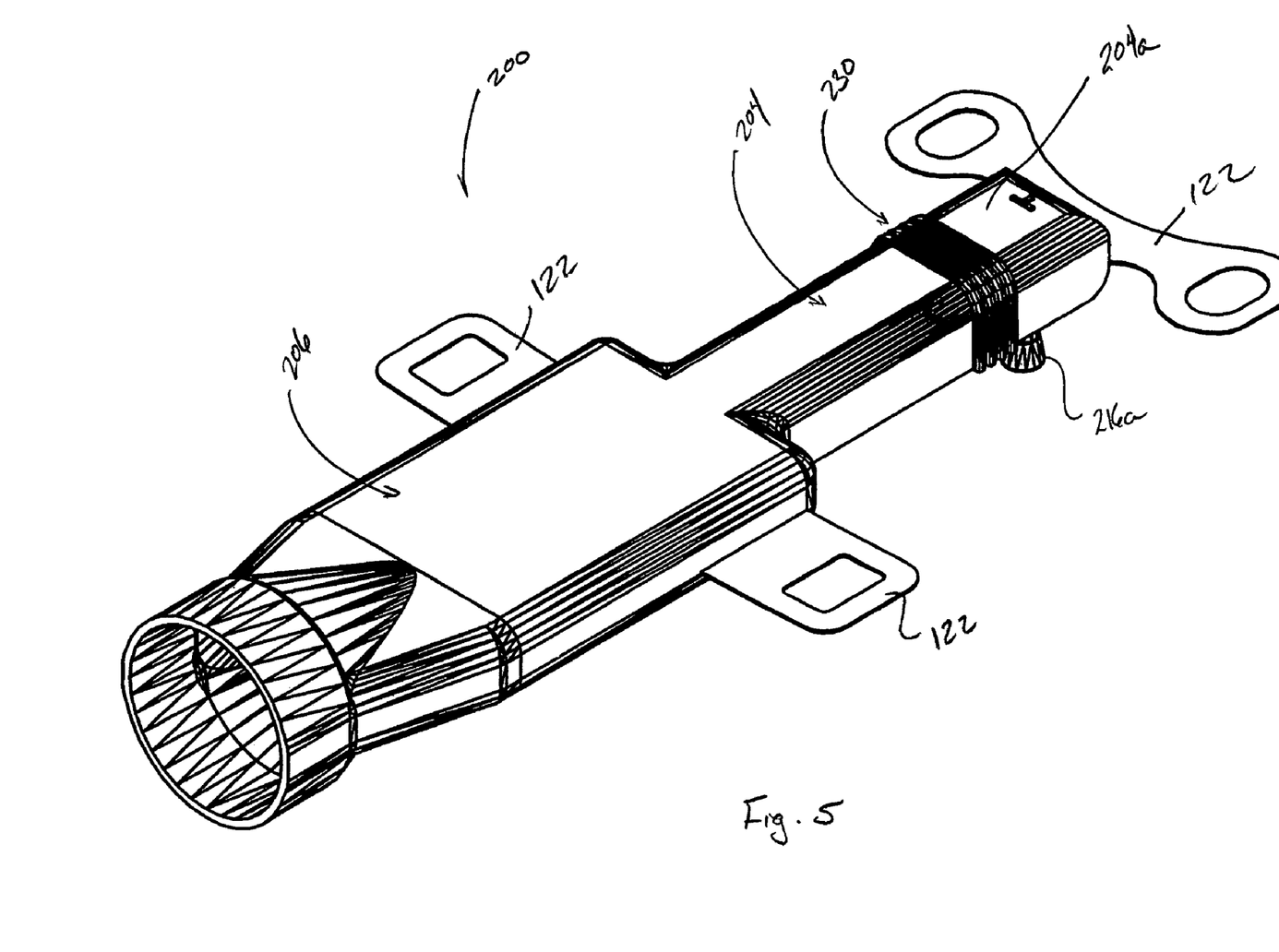
FIG. 5 is a perspective view of a continuous positive airway pressure system in accordance with another embodiment of the present disclosure.
Figure 6:
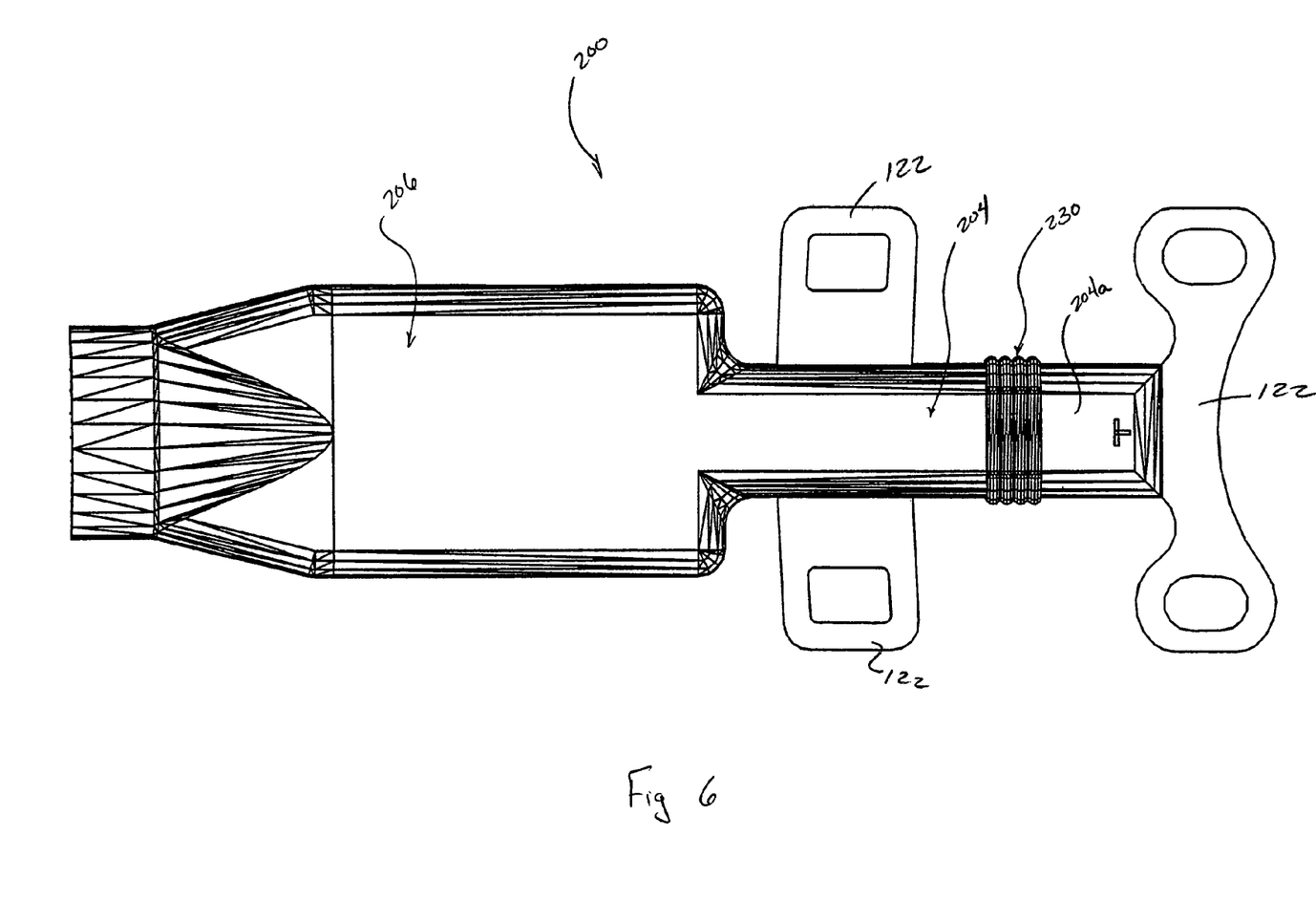
FIG. 6 is a top plan view of the continuous positive airway pressure system of FIG. 5.
Figure 7:
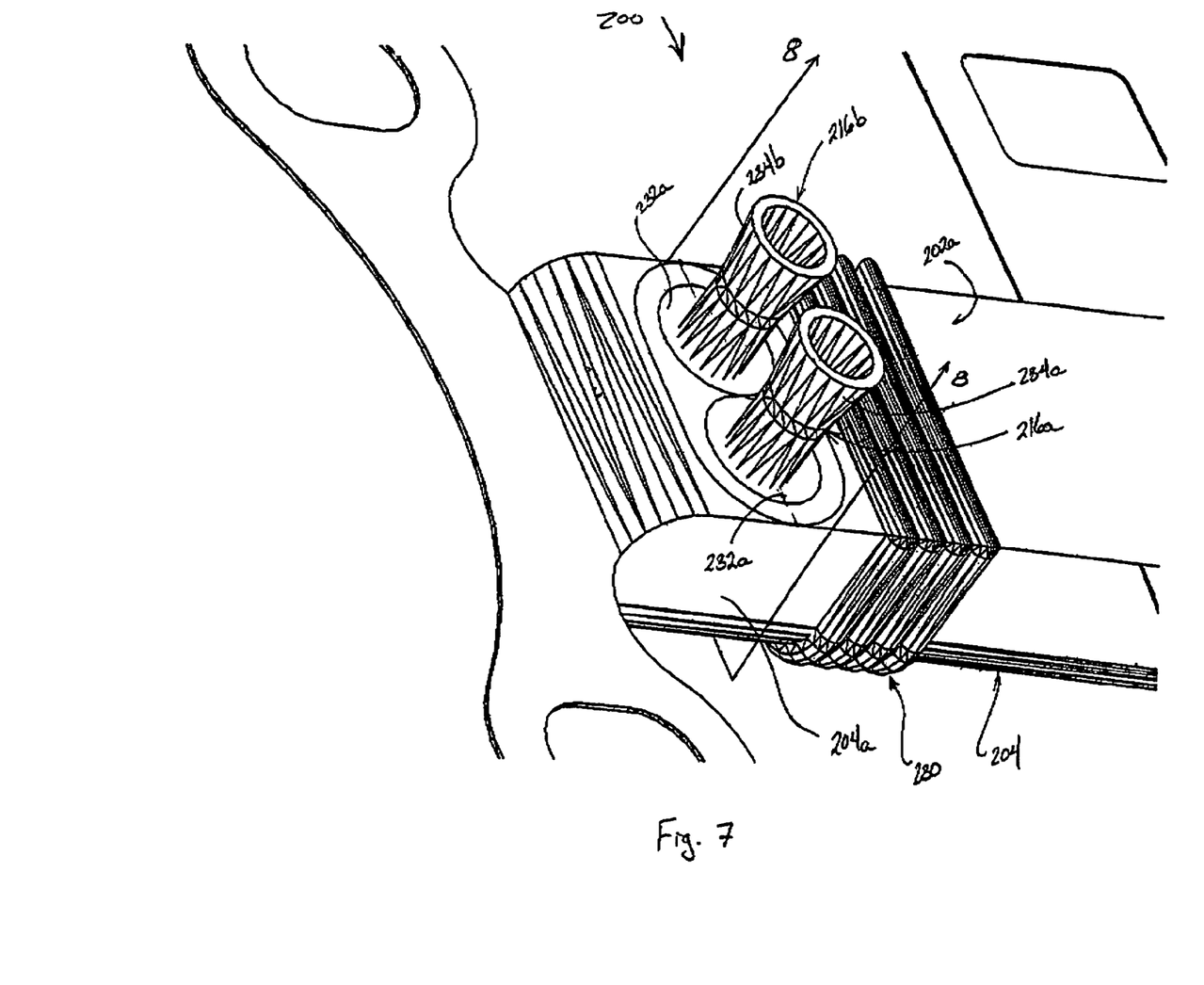
FIG. 7 is an enlarged perspective view of the distal end of the continuous positive airway pressure system of FIGS. 5–6 as seen from below.

As seen in FIGS. 5–7, continuous positive airway pressure system 200 includes a corrugated section and/or an accordion-like section 230 formed in proximal end portion 204. Accordion-like section 230 permits a proximal-most end 204a of proximal end portion 204 to be deflected and/or bent off axis relative to the longitudinal axis of continuous positive airway pressure system 200. In this manner, accordion-like section 230 permits proximal end portion 204 to better to conform to the contours of the face of infant "I" and to reduce the tendency of proximal end portion 204 from crimping along the length thereof.

Figure 8:
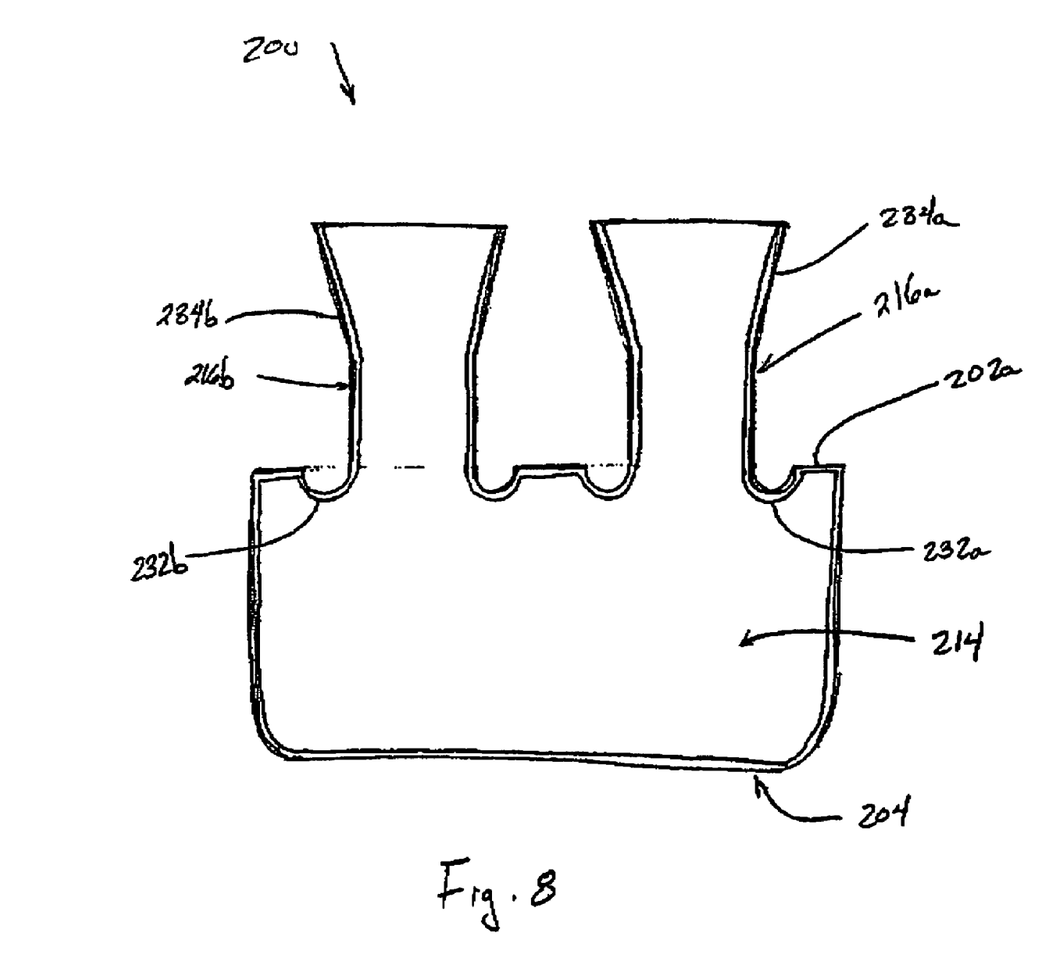
FIG. 8 is a cross-sectional view of the continuous positive airway pressure system of FIGS. 5–7 as taken through 8—8 of FIG. 7.

As seen in particular in FIGS. 7 and 8, continuous positive airway pressure system 200 includes a pair of nasal cannulas 216a, 216b extending from a lower surface 202a thereof. Preferably, each nasal cannula 216a, 216b is surrounded by an annular trough or donut-like recess 232a, 232b, respectively, formed in lower surface 202a. Preferably, the thickness of the material making up recesses 232a, 232b is less than the thickness of continuous positive airway pressure system 200. In this manner, recesses 232a, 232b gives nasal cannulas 216a, 216b the ability to move and/or pivot off axis without kinking.

Figure 3:
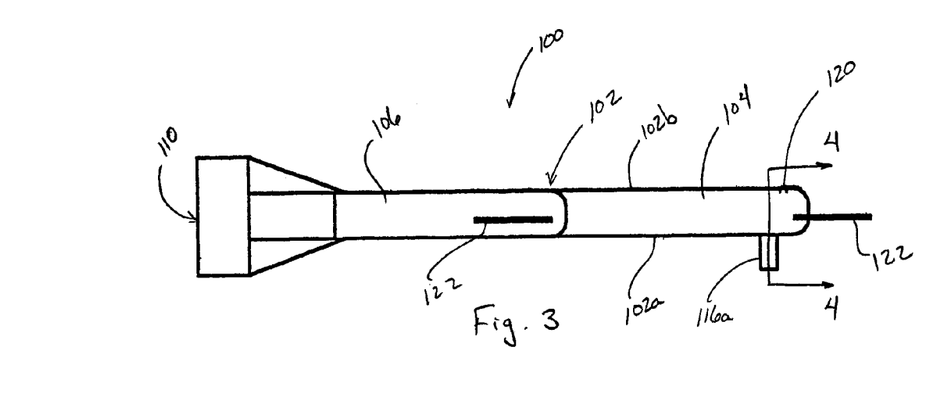
FIG. 3 is a side elevational view of the continuous positive airway pressure system of FIGS. 1–2.
Figure 4:
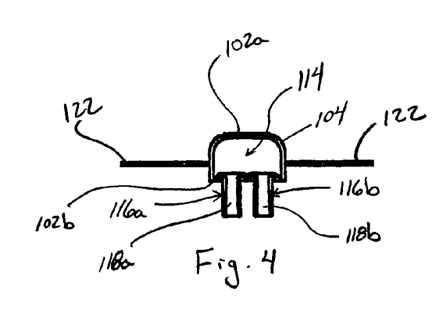
FIG. 4 is a cross-sectional view of the continuous positive airway pressure system of FIGS. 1–3 as taken through 4—4 of FIG. 3.

Preferably, as seen in FIGS. 7 and 8, each nasal cannula 216a, 216b can have a flared/fluted/frusto-conical distal end portion 234a, 234b, respectively. Flared distal end portions 234a, 234b are sized and dimensioned to substantially fill the nares of infant "I". In this manner, substantially all the air respired by infant "I" is supplied by continuous positive airway pressure system 200. While nasal cannulas 216a, 216b are shown as being flared in FIGS. 7 and 8, it is envisioned and within the scope of the t disclosure that nasal cannulas 216a, 216b can be cylindrical as shown in FIGS. 3 and 4.

Figure 9:
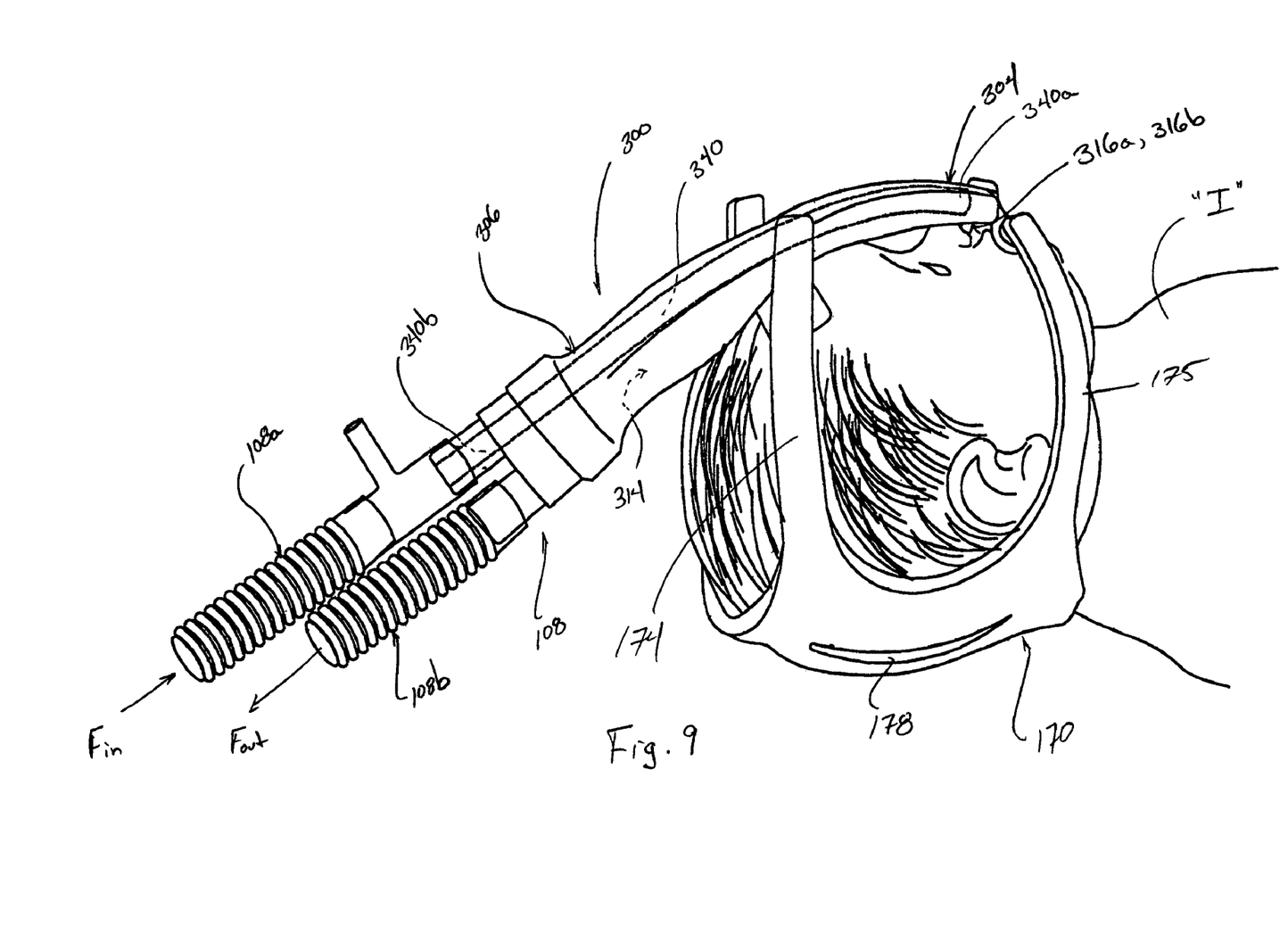
FIG. 9 is a perspective view of a continuous positive airway pressure system in accordance with yet another embodiment of the present disclosure, supported on the head of a patient and/or infant.

With reference to FIG. 9, a continuous positive airway pressure system in accordance with an alternate embodiment of the present disclosure is shown generally as 300. Continuous positive airway pressure system 300 is similar to continuous positive airway pressure systems 100 and 200 and will only be described in detail to the extent necessary to identify differences in construction and use.

As seen in FIG. 9, continuous positive airway pressure system 300 further includes an internal conduit 340 extending from distal end portion 306, through plenum chamber 314, substantially to proximal end portion 304. Preferably, proximal end 340a of conduit 340 terminates at a location distal of nasal cannulas 316a, 316b. Internal conduit 340 is preferably fabricated from a flexible resilient material, such as, for example, silicone, rubber and the like. In this manner, internal conduit 340 does not interfere with the flexibility of continuous positive airway pressure system 300.

It is envisioned that internal conduit 340 can be provided with at least a region of corrugation and/or at least a portion which is accordion-like to thereby increase the bendability of internal conduit 340 prior to kinking.

Preferably, distal end 340b of conduit 340 is in fluid engagement with first ventilation tube 108a of ventilation circuit 108. In this manner, air flow $F_{in}$ is directly transmitted substantially to proximal end portion 304 of continuous positive airway pressure system 300. Continuous positive airway pressure system 300 preferably does not include an exhalation vent formed in proximal end portion 304 thereof. In this manner, substantially all of air flow $F_{out}$ is directed out of continuous positive airway pressure system 300 through second ventilation tube 108b.

In use, infant "I" inhales air from expanded pressurized interface 302 through nasal cannulas 316a, 316b and exhales back into interface 102. Since internal conduit 340 substantially delivers air flow $F_{in}$ directly to nasal cannulas 316a, 316b, infant "I" substantially only inhales air supplied from air pressure source "P" (see FIG. 1). When infant "I" exhales, the exhaled air is transmitted out of interface 102 through second ventilation tube 108b fluidly coupled to ventilation circuit 108.

With reference to FIGS. 10–19, a continuous positive airway pressure system in accordance with an alternate embodiment of the present disclosure is shown generally as 400. Continuous positive airway pressure system 400 is similar to continuous positive airway pressure systems 100, 200 and 300 and will only be described in detail to the extent necessary to identify differences in construction and use.

As seen in FIGS. 10–15, continuous positive airway pressure system 400 includes an air inlet 450 in fluid communication with plenum chamber 414 of continuous positive airway pressure system 400. Air inlet 450 is configured and adapted to be fluidly coupled to ventilation circuit 108.

Continuous positive airway pressure system 400 further includes a vent cover 452 overlying exhalation vent 420. Vent cover 452 is a safety feature that acts as protection against inadvertent obstruction while allowing gas to freely exit plenum chamber 414 of continuous positive airway system 400. Preferably, vent cover 452 is fabricated from a mesh-like material or fabric that is difficult to occlude.

With reference to FIGS. 12–19 and in particular FIGS. 16–19, continuous positive airway pressure system 400 includes a nasal cannula assembly 460 operatively associated with proximal end portion 406 thereof. Cannula assembly 460 includes a base 462, a pair of nasal cannulas 416a, 416b extending substantially orthogonally from base 462, and a plurality of support stems 464 extending orthogonally from base 462 on a side opposite the pair of nasal cannulas 416a, 416b.

Preferably, each nasal cannula 416a, 416b is supported on base 462 in the same manner nasal cannulas 216a, 216b of continuous positive airway pressure system 200 above. In particular, each cannula 416a, 416b is surrounded by an annular trough or dough-nut like recess 432a, 432b, respectively, formed in base 462. In this manner, recesses 432a, 432b give nasal cannulas 416a, 416b the ability to move and/or pivot off axis without kinking.

Support stems 464 are preferably positioned along the perimeter of base 462. Support stems 464 extend from base 462 an amount sufficient to maintain upper surface 402b spaced a distance away from lumens 418a, 418b of nasal cannulas 416a, 416b in the event there is a no-flow, no-pressure condition wherein interface 402 of continuous positive airway pressure system 400 would deflate (see FIG. 14) and upper surface 402b would lie over lumens 418a, 418b and prevent passage of any air flow to infant "I". In effect, support stems 464 function as a safety feature in the event that there is a no-flow, no-pressure condition.

As seen in FIGS. 1, 9, 10 and 20, a bonnet 170 is provided for securing continuous positive airway pressure systems 100, 200, 300 or 400 (in the interest of clarity, hereinafter referred to as continuous positive airway pressure system 100) to the head of infant "I". Bonnet 170 includes a body section 172, an upper set of straps 174, 175 extending in opposed directions from body section 172, and a lower set of straps 176, 177 extending in opposed directions from body section 172.

Body section 172 includes at least one, preferably a series of elongate slits 178 formed therein. Preferably, slits 178 are oriented in a direction orthogonal to the direction of straps 174–177. In this manner, as bonnet 170 is placed against the head of infant "I", slits 178 expand, the direction of arrows "A" of FIG. 20, in order to accommodate the curvature of the head of infant "I" (as seen in FIGS. 1 and 9).

A respective distal end portion 174a–177a, of each strap 174–177 is preferably provided with the other of hook or loop portion 124b for releasably engaging the hook or loop portion 124a of each tab 122 of continuous positive airway pressure system 100. While a hook and loop type fastener is preferred, it is envisioned that other types of fastening elements can be used to releasably secure bonnet 170 to continuous positive airway pressure system 100, such as, for example, and not limited to, the tying of the ends of straps, use of a belt-like configuration, elastic bands extending from continuous positive airway pressure system 100 and the like.

Bonnet 170 is preferably fabricated from a soft material, such as, for example, a open cell foam, that easily conforms to the shape of the head of infant "I" while providing sufficient tensile strength to support continuous positive airway pressure system 100 on the face of infant "I". Bonnet 170 can further be provided with an inner and/or an outer layer of covering material and/or fabric for providing greater comfort to infant "I".

Figure 10:
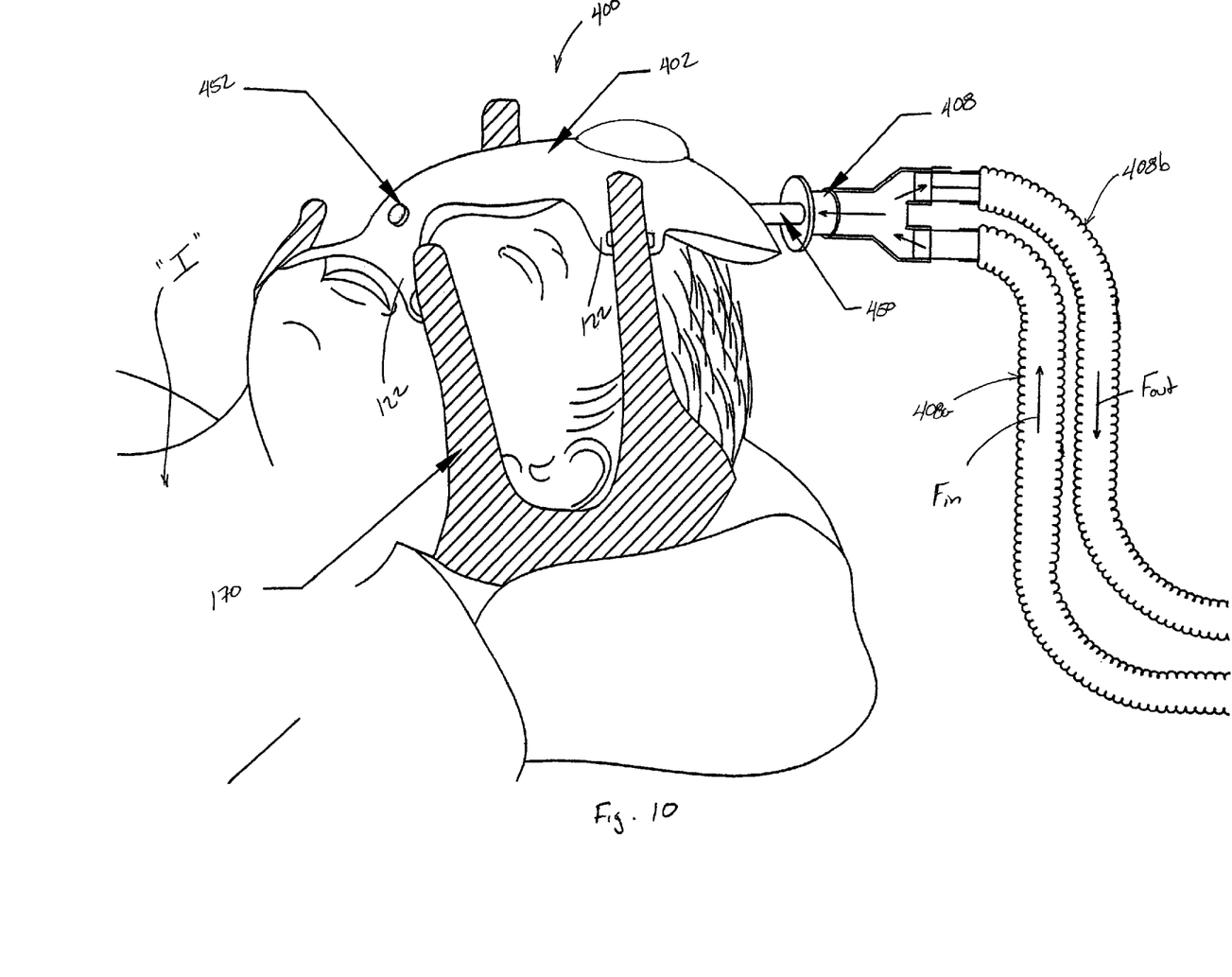
FIG. 10 is a perspective view of a continuous positive airway pressure system in accordance with still another embodiment of the present disclosure, supported on the head of a patient and/or infant.
Figure 11:
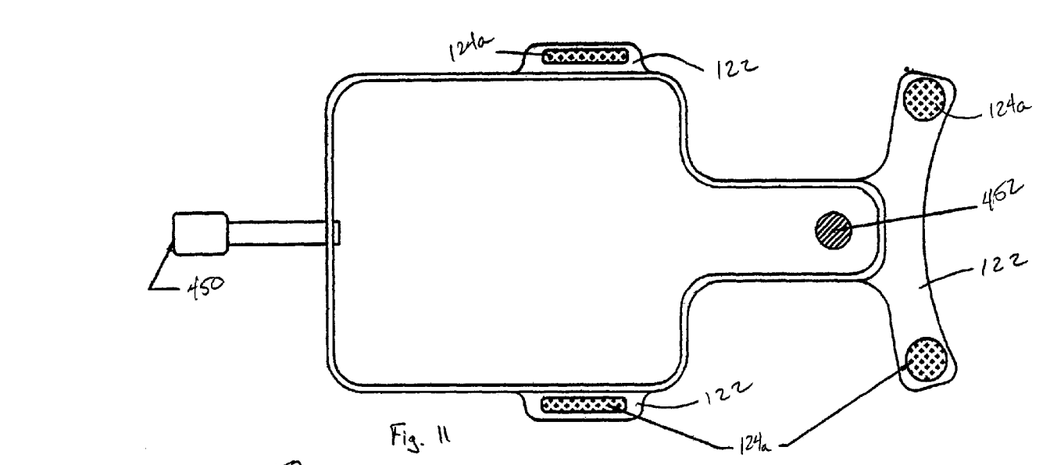
FIG. 11 is a top plan view of the continuous positive airway pressure system of FIG. 10.
Figure 12:
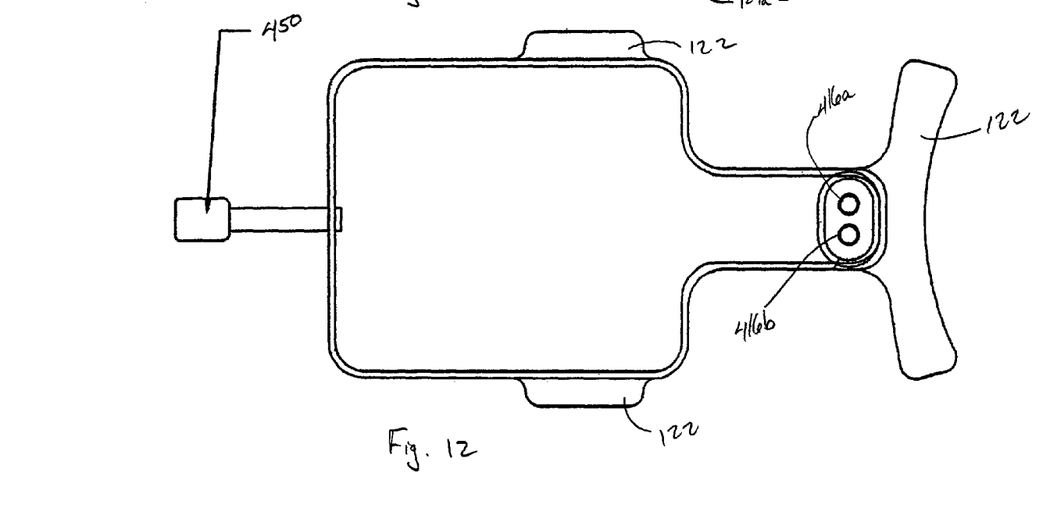
FIG. 12 is a bottom plan view of the continuous positive airway pressure system of FIGS. 10 and 11.
Figure 13:
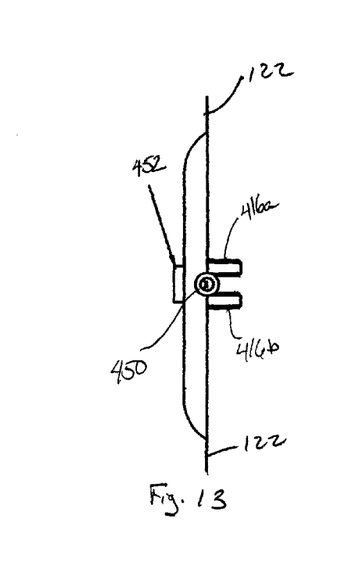
FIG. 13 is a front end view of the continuous positive airway pressure system of FIGS. 10–12.
Figures 14, 15, 16:
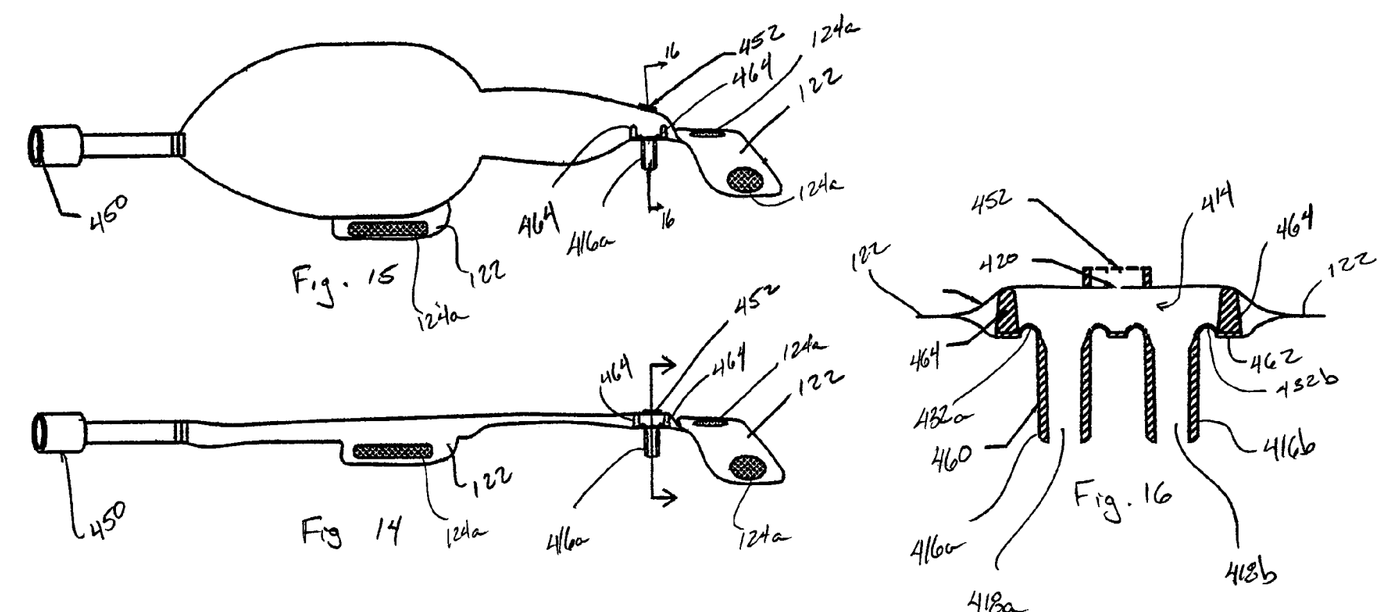
FIG. 14 is a side elevational view of the continuous positive airway pressure system of FIGS. 10–13.
FIG. 15 is a side elevational view of the continuous positive airway pressure system of FIGS. 10–14 while under pressure.
FIG. 16 is a cross-sectional view of the continuous positive airway pressure system of FIGS. 10–15 as taken through 16—16 of FIG. 15.
Figure 17:
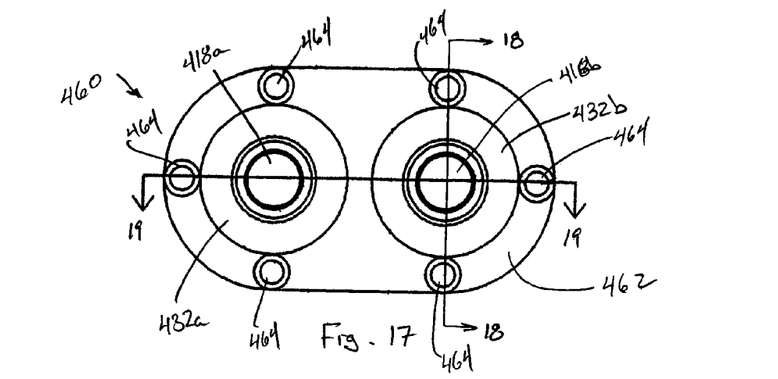
FIG. 17 is a top plan view of a nasal cannula base in accordance with an embodiment of the present disclosure.
Figure 18:
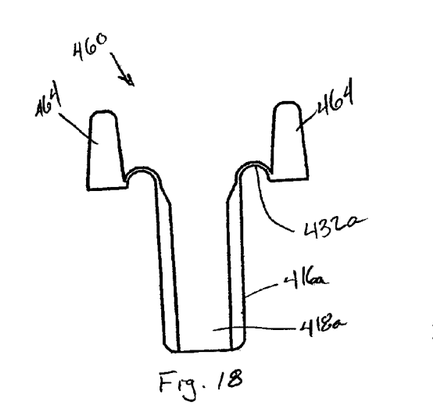
FIG. 18 is a cross-sectional view of the cannula base of FIG. 17 as taken through 18—18 of FIG. 17.
Figure 19:
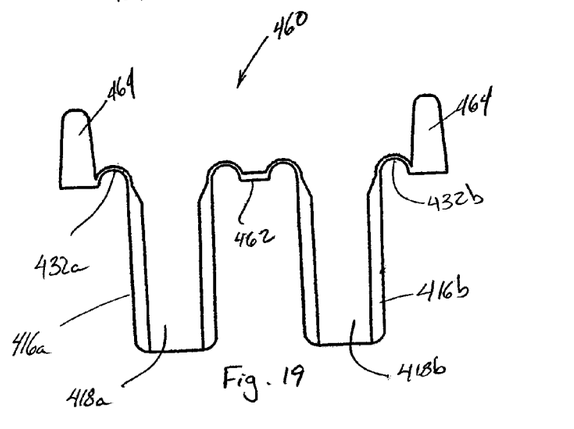
FIG. 19 is a cross-sectional view of the cannula base of FIG. 17 as taken through 19—19 of FIG. 17.
Figure 20:
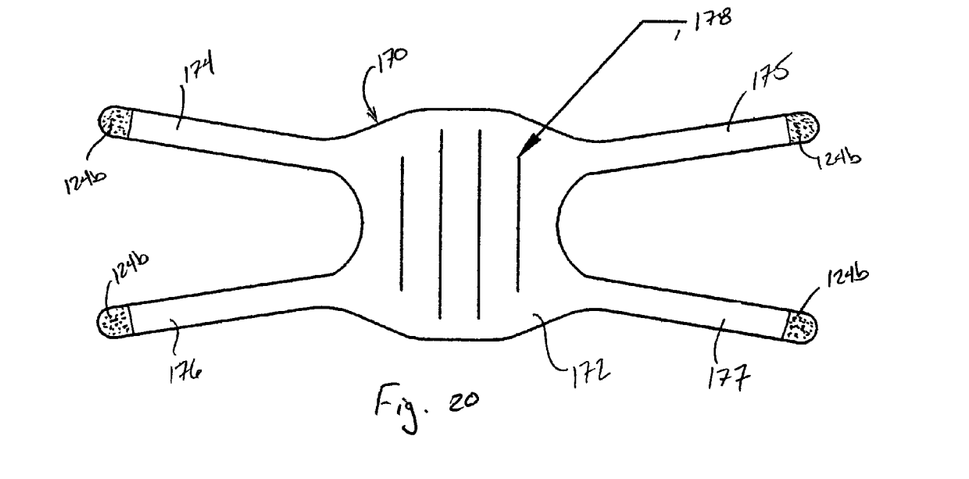
FIG. 20 is a top plan view of a bonnet in accordance with the present disclosure.

With reference to FIG. 10, it is envisioned that continuous positive airway pressure system 400 can be fabricated from a non-elastic material and include a portion or window of elastic material 401 having sufficient elasticity to enhance and/or supplement the air pressure within the plenum chamber.

While particular embodiments of the present disclosure have been described, it will be evident to those skilled in the art that the present disclosure may be embodied in other specific forms without departing from the essential characteristics thereof.

For example, while the interfaces of continuous positive airway pressure systems 100, 200, 300 and 400 have been shown and described as being elastic throughout, it is envisioned and within the scope of the present disclosure that only certain portions, areas and/or sections of the interfaces need to be elastic, such as, for example, in the form of a window, the upper half, the lower half, the distal end portion, the proximal end portion and/or any combination thereof.

The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A continuous positive airway pressure system, comprising:
   an interface defining a plenum chamber therein, wherein the interface is connectable to a ventilation circuit for delivering pressurized air to the plenum chamber; and
   a pair of nasal cannulas in fluid communication with the interface, each nasal cannula including a free end portion and a base portion, each nasal cannula being integrally connected to the interface via an annular trough extending from the base end portion of the nasal cannula to a surface of the interface, wherein each annular trough extends completely around a respective one of the nasal cannulas, wherein each annular trough has a thickness which is less than a thickness of the surface of the interface, the nasal cannulas being configured and dimensioned to deliver pressurized air to the nares of a patient, wherein the annular troughs allow for each nasal cannula to at least one of move and pivot off axis.

2. The continuous positive airway pressure system of claim 1, wherein at least a portion of the interface is fabricated from elastic material.

3. The continuous positive airway pressure system of claim 2, further including a conduit internally disposed within the interface, wherein the conduit extends from the ventilation circuit to a location in close proximity to the nasal cannulas.

4. The continuous positive airway pressure system of claim 3, wherein the conduit is flexible.

5. The continuous positive airway pressure system of claim 3, further comprising an exhalation vent formed in a distal end of the interface.

6. The continuous positive airway pressure system of claim 5, wherein the exhalation vent is sized to allow more than two times the exhalation volume of the patient to pass therethrough on each exhalation of the patient.

7. The continuous positive airway pressure system of claim 6, further comprising a vent cover overlying the exhalation vent.

8. The continuous positive airway pressure system of claim 6, further comprising support stems disposed within the interface and about the nasal cannulas for maintaining the nasal cannulas in fluid communication with the plenum chamber.

9. The continuous positive airway pressure system of claim 6, further including a bonnet for mounting the system to the head of the patient.

10. The continuous positive airway pressure system of claim 9, wherein the bonnet includes a body portion and straps extending therefrom, the body portion including at least one slit formed therein.

11. The continuous positive airway pressure system of claim 10, wherein each strap includes one portion of a hook and loop fastener and the interface includes the other portion of the hook and loop fastener for releasably engaging the one portion of the hook and loop fastener.

12. The continuous positive airway pressure system of claim 1, wherein the free end portion of each nasal cannula is fluted.

13. The continuous positive airway pressure system of claim 2, wherein the interface is fabricated from silicone.

* * * * *